United States Patent
Miao et al.

(10) Patent No.: US 12,336,546 B2
(45) Date of Patent: Jun. 24, 2025

(54) ANTIBACTERIAL GLUCOSE-BASED COMPOSITE NANOPARTICLE AND PROCESSING METHOD AND USE THEREOF

(71) Applicant: Jiangnan University, Wuxi (CN)

(72) Inventors: Ming Miao, Wuxi (CN); Yao Liu, Wuxi (CN); Chaohui Zhi, Wuxi (CN); Tao Zhang, Wuxi (CN); Zhengyu Jin, Wuxi (CN)

(73) Assignee: Jiangnan University, Wuxi (CN)

( * ) Notice: Subject to any disclaimer, the term of this patent is extended or adjusted under 35 U.S.C. 154(b) by 460 days.

(21) Appl. No.: 17/744,811

(22) Filed: May 16, 2022

(65) Prior Publication Data

US 2022/0273004 A1   Sep. 1, 2022

Related U.S. Application Data

(63) Continuation of application No. PCT/CN2020/129605, filed on Nov. 18, 2020.

(30) Foreign Application Priority Data

Nov. 19, 2019 (CN) .......................... 201911134115.9

(51) Int. Cl.
*A23B 2/729* (2025.01)
*A23B 2/783* (2025.01)
(Continued)

(52) U.S. Cl.
CPC ............ *A23B 2/7295* (2025.01); *A23B 2/783* (2025.01); *A61Q 17/005* (2013.01); *B82Y 5/00* (2013.01)

(58) Field of Classification Search
CPC ........ A23L 3/3571; A61Q 17/005; B82Y 5/00
See application file for complete search history.

(56) References Cited

FOREIGN PATENT DOCUMENTS

BR   102016010730 A2 * 11/2017
CN      102726729 A    10/2012
(Continued)

OTHER PUBLICATIONS

Machine translation provided from PE2E via FIT of BR 102016010730-A2 (Year: 2017).*

(Continued)

*Primary Examiner* — Bethany P Barham
*Assistant Examiner* — Ayaan A Alam
(74) *Attorney, Agent, or Firm* — IPRO, PLLC

(57) ABSTRACT

The present disclosure discloses an antibacterial glucose-based composite nanoparticle and a processing method and use thereof, and belongs to the technical field of processing of modern food. According to the present disclosure, the antibacterial composite nanoparticle is prepared by using a particle surface positioning modification technology and a physical field charge transfer technology with a natural glucose-based nanoparticle as a raw material. The obtained antibacterial composite nanoparticle has a particle size of 50-1,000 nm, a surface zeta potential of 0 to −10 mV and a broad-spectrum antibacterial rate of greater than 98%. The shelf life of food can be effectively prolonged to prevent spoilage of products. The antibacterial composite nanoparticle can be used in food, textiles, daily chemicals, medicine and many other fields, and has a wide application prospect.

8 Claims, 1 Drawing Sheet

(51) Int. Cl.
 *A61Q 17/00* (2006.01)
 *B82Y 5/00* (2011.01)

(56) References Cited

FOREIGN PATENT DOCUMENTS

| | | |
|---|---|---|
| CN | 102924623 A | 2/2013 |
| CN | 108424942 A | 8/2018 |
| CN | 110859184 A | 3/2020 |

OTHER PUBLICATIONS

Bi Lin et al., "Designing carbohydrate nanoparticles for prolonged efficacy of antimicrobial peptide", Journal of Controlled Release, V150, Issue 2, Nov. 27, 2010, p. 150-156.

\* cited by examiner

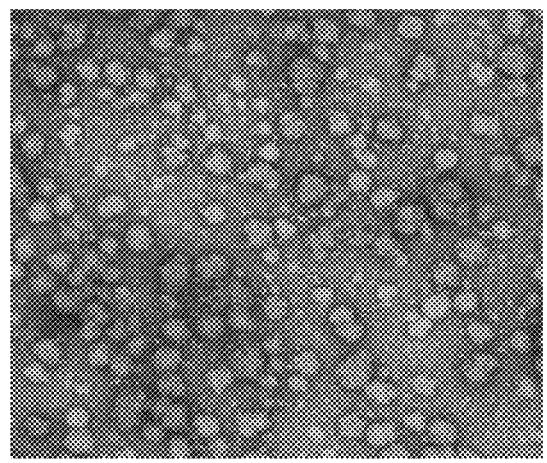

ANTIBACTERIAL GLUCOSE-BASED COMPOSITE NANOPARTICLE AND PROCESSING METHOD AND USE THEREOF

TECHNICAL FIELD

The present disclosure relates to an antibacterial glucose-based composite nanoparticle and a processing method and use thereof, and belongs to the technical field of processing of modern food.

BACKGROUND

As a new advanced high technology obtained and rapidly developed in the late 1980s, a nanotechnology is a highly interdisciplinary subject involving modern physics, chemistry, biology, medicine, material science, information science, energy science and advanced manufacturing science. The nanotechnology is used for studying properties and use of nanometer materials (usually 1-100 nm). By using the nanotechnology, means and ability of human beings to understand and transform the material world are expanded to an atomic level and a molecular level. Nanometer substances have the characteristics of a quantum size effect, a surface effect and a macroscopic quantum tunneling effect, and some characteristics that are different from or not available to macroscopic substances in physics, chemistry, optics, mechanics, biology and the like. At present, the nanotechnology has made a profound impact on the world, and is gradually used in the fields of food, agriculture, medicine and other traditional industries. In developed countries in Europe and America, a lot of manpower and material resources have been invested in research and development of a series of nanometer products, such as active factor nanocarriers, antibacterial food packaging products, nanoencapsulated chemical inputs, nanoemulsions and nanosensors.

In recent years, due to overuse of antibiotics, there are increasing multidrug-resistant strains in the world. As a result, more and more attention has been paid to research of new efficient antibacterial agents. Metal and metal oxide nanoparticles, such as Ag, $TiO_2$, ZnO and $Fe_3O_4$, have efficient antibacterial activity, and are used for destroying cell walls or cell membranes of bacteria, blocking electron transfer across membranes and inhibiting enzyme activity and DNA synthesis. However, these antibacterial nanoparticles have problems such as low safety, high cost and poor efficacy. For example, the Ag nanoparticles and the $TiO_2$ nanoparticles both have a certain degree of toxicity, which may have a negative impact on human health and the environment. In addition, there are few reports on preparation of antibacterial nanoparticles by using natural biodegradable biomacromolecules, and until now, there are no reports on antibacterial glucose-based composite nanoparticles. Based on the reasons above, in order to expand the use field and increase the added value of natural nanomaterials, it is urgent to develop a processing method and use of an antibacterial glucose-based composite nanoparticle.

SUMMARY

In order to solve the problems above, the present disclosure provides an antibacterial glucose-based composite nanoparticle. The antibacterial glucose-based composite nanoparticle of the present disclosure has excellent antibacterial properties, and can be used as a matrix material in the fields of food, textiles, daily chemicals and medicine. The method has the characteristics of simple technology, controllable process and environmental protection.

A first objective of the present disclosure is to provide a processing method of an antibacterial glucose-based composite nanoparticle. The method includes the following steps:

(1) dispersing a natural glucose-based nanoparticle in water, and adding a microbial GH13 family glucoside hydrolase that is 50-200 U/g of the natural glucose-based nanoparticle for a catalytic reaction;

(2) after the reaction is completed, adding an organic acid anhydride esterification agent and an etherification agent, and adjusting the pH to 7-13 for a reaction in a microwave environment; and (3) after the reaction is completed, adding a preservative of 0.01-1% by mass of the natural glucose-based nanoparticle for a reaction in an ultrasonic environment, and then taking precipitation and drying.

In an embodiment of the present disclosure, the natural glucose-based nanoparticle is derived from a plant, an animal or a microorganism, the plant and animal sources are obtained by extracting some tissues from cereal grains, algae and animals in a growing period, and the microorganism source is obtained by extracting bacteria after activated culture and fermentation. An obtained product has a molecular weight of $10^6$-$10^8$ g/mol and a dispersed molecular density of 1,000-2,000 g/(mol·nm$^3$).

In an embodiment of the present disclosure, in step (1), the natural glucose-based nanoparticle in the water has a mass concentration of 10-40%.

In an embodiment of the present disclosure, in step (1), the catalytic reaction is carried out at a constant temperature of 30-70° C. and a pH of 3.5-7.0 for 0.5-12 h.

In an embodiment of the present disclosure, the microbial GH13 family glucoside hydrolase includes one or more selected from the group consisting of maltosidase, amyloglucosidase and starch hydrolase.

In an embodiment of the present disclosure, the organic acid anhydride esterification agent includes one or more selected from the group consisting of succinic anhydride, maleic anhydride, acetic anhydride, stearic anhydride and citric anhydride, and the etherification agent includes one or more selected from the group consisting of epichlorohydrin, oxirene, methyl chloride, ethyl chloride and dimethylsulfuric acid.

In an embodiment of the present disclosure, in step (2), the organic acid anhydride esterification agent is added in an amount of 0.5-3% of the mass of the natural glucose-based nanoparticle.

In an embodiment of the present disclosure, in step (2), the etherification agent is added in an amount of 1-10% of the mass of the natural glucose-based nanoparticle.

In an embodiment of the present disclosure, in step (2), a microwave powder is adjusted to 400-1,000 W; and in step (2), the reaction is carried out at 30-50° C. for 1-10 h.

In an embodiment of the present disclosure, the preservative includes one or more selected from the group consisting of nisin, lysozyme, chitin, ε-polylysine, natamycin, thymol, eugenol and Gemini quaternary ammonium salts.

In an embodiment of the present disclosure, in step (3), an ultrasonic frequency is 20-100 kHz; and in step (3), the reaction is carried out at 20-50° C. for 0.1-5 h to realize charge transfer.

A second objective of the present disclosure is to provide an antibacterial glucose-based composite nanoparticle prepared by using the method above.

A third objective of the present disclosure is to provide use of the antibacterial glucose-based composite nanoarticle in active food packaging, cosmetics, textiles, hydrogels and adhesives.

The present disclosure has the following advantages.

1. The present disclosure has wide sources of raw materials, including grains, algae, animals and microorganisms, which are not restricted by the origin and season.

2. The antibacterial composite nanoparticle is prepared by using a particle surface positioning modification technology and a physical field charge transfer technology with the natural glucose-based nanoparticle as a raw material. After the antibacterial composite nanoparticle is used in antibacterial films and other surface contact packaging products, the shelf life of food can be effectively prolonged to prevent spoilage of products.

3. The antibacterial glucose-based composite nanoparticle has a particle size of 50-1,000 nm, a surface zeta potential of 0 to −10 mV and a broad-spectrum antibacterial rate of greater than 98%, and can be used in food, textiles, daily chemicals, medicine and many other fields. For example, the antibacterial glucose-based composite nanoparticle has an application prospect in active food packaging, cosmetics, textiles, hydrogels and adhesives.

BRIEF DESCRIPTION OF FIGURES

FIG. 1 is an electron microscope photograph (bar 100 nm) of an antibacterial glucose-based composite nanoparticle obtained in Example 1.

DETAILED DESCRIPTION

A measurement method of a broad-spectrum antibacterial rate is as follows.

*Escherichia coli, Staphylococcus aureus, Salmonella typhimurium, Listeria monocytogenes* and other food-borne spoilage bacteria are subjected to streak culture on a nutrient agar culture medium at 37° C. for 12 h. A single colony is picked, cultured in a nutrient broth culture medium at 37° C. for 12 h, and then subjected to plate counting. A certain amount of a bacterial liquid is sucked into 100 mL of a nutrient broth culture medium (with a finally number of 107 CFU/mL). Then, an appropriate amount of an antibacterial glucose-based composite nanoparticle is added to obtain a mixture. Next, the mixture is cultured in a constant-temperature incubator at 37° C. Samples are measured at 0 h, 4 h, 6 h, 8 h, 10 h, 12 h and 24 h to obtain an OD600 value. The sample cultured for 12 h is subjected to plate counting and then measured to obtain an antibacterial rate. Three parallel tests are carried out on each sample, and a calculation formula is as follows:

$$\text{antibacterial rate (\%)} = (OD600_{blank} - OD600_{sample})/OD600_{blank},$$

where, the $OD600_{blank}$ refers to an OD600 value when the antibacterial glucose-based composite nanoparticle is not added, and the $OD600_{sample}$ refers to an OD600 value when the antibacterial glucose-based composite nanoparticle is added.

A measurement method of a surface zeta potential is as follows.

A to-be-tested antibacterial glucose-based composite nanoparticle is prepared into a 0.1% (w/v) solution, and then measured by using a Malvern Nano ZS tester at 25° C. to obtain a surface zeta potential.

A natural glucose-based nanoparticle may be obtained by extracting some tissues from cereal grains, algae and animals in a growing period by using an existing technology, or extracting a microorganism from bacteria after activated culture and fermentation. Specifically, the antibacterial glucose-based composite nanoparticle may be prepared with reference to the following literature: Structure and digestibility of endosperm water-soluble a-glucans from different sugary maize mutants, Food Chemistry 143 (2014) 156-162.

Example 1

A glucose-based nanoparticle (with a molecular weight of $2.3*10^7$ g/mol and a dispersed molecular density of 1,230 g/(mol·nm³)) derived from oysters was weighed and prepared into a homogeneous aqueous solution with a mass concentration of 40%. A microbial GH13 family amyloglucosidase that was 200 U/g of the substrate was added. Parameters of a reaction system were adjusted as follows: the temperature was 50° C., the pH was 7.0, and constant-temperature catalysis was conducted for 0.5 h. Succinic anhydride was added in an amount of 0.5% of a mass of the substrate, oxirene was added in an amount of 3% of the mass of the substrate, and the pH of a reaction system was adjusted to 12. Then, a microwave-assisted processing technology was used for adjusting a microwave power to 800 W to carry out a reaction at 50° C. for 6 h. Next, chitin was added in an amount of 0.01% of the mass of the substrate, and a physical field charge transfer technology was used for adjusting an ultrasonic frequency to 100 kHz to carry out a reaction at 20° C. for 0.5 h. Finally, precipitation and drying were conducted to obtain a target product.

The obtained target product had an average particle size of 110 nm, a surface zeta potential of −5.2 mV and a broad-spectrum antibacterial rate of 98.7%.

Example 2

A glucose-based nanoparticle (with a molecular weight of $7.3*10^6$ g/mol and a dispersed molecular density of 1,510 g/(mol·nm³)) derived from rice was weighed and prepared into a homogeneous aqueous solution with a mass concentration of 10%. A microbial GH13 family maltosidase that was 50 U/g of the substrate was added. Parameters of a reaction system were adjusted as follows: the temperature was 30° C., the pH was 6.0, and constant-temperature catalysis was conducted for 8 h. Acetic anhydride was added in an amount of 3% of a mass of the substrate, oxirene was added in an amount of 1% of the mass of the substrate, and the pH of a reaction system was adjusted to 10. Then, a microwave-assisted processing technology was used for adjusting a microwave power to 400 W to carry out a reaction at 30° C. for 10 h. Next, nisin was added in an amount of 0.5% of the mass of the substrate, and a physical field charge transfer technology was used for adjusting an ultrasonic frequency to 50 kHz to carry out a reaction at 50° C. for 2 h. Finally, precipitation and drying were conducted to obtain a target product.

The obtained target product had an average particle size of 170 nm, a surface zeta potential of −7.5 mV and a broad-spectrum antibacterial rate of 99.4%.

Example 3

A glucose-based nanoparticle (with a molecular weight of $1.8*10^6$ g/mol and a dispersed molecular density of 1,080 g/(mol·nm³)) derived from *Kluyveromyces marxianus* was weighed and prepared into a homogeneous aqueous solution with a mass concentration of 20%. A microbial GH13 family maltosidase that was 100 U/g of the substrate was added. Parameters of a reaction system were adjusted as follows: the temperature was 60° C., the pH was 5.0, and constant-temperature catalysis was conducted for 2 h. Maleic anhydride was added in an amount of 1% of a mass of the substrate, ethyl chloride was added in an amount of 5% of the mass of the substrate, and the pH of a reaction system was adjusted to 8. Then, a microwave-assisted processing technology was used for adjusting a microwave power to 500 W to carry out a reaction at 35° C. for 3 h. Next, lysozyme was added in an amount of 1% of the mass of the substrate, and a physical field charge transfer technology was used for adjusting an ultrasonic frequency to 80 kHz to carry out a reaction at 30° C. for 1 h. Finally, precipitation and drying were conducted to obtain a target product.

The obtained target product had an average particle size of 290 nm, a surface zeta potential of −1.2 mV and a broad-spectrum antibacterial rate of 99.3%.

Example 4 Optimization of Use Amount of Enzyme

With reference to Example 1, corresponding composite particles were separately prepared by changing the use amount of a microbial GH13 family glucoside hydrolase into 30 U/g and 300 U/g when other conditions were unchanged. Properties of the composite particles were measured, and results were shown in Table 1.

TABLE 1

Results of properties of composite particles prepared with different use amounts of an enzyme

| Use amount of enzyme (U/g) | Surface zeta potential (mV) | Antibacterial rate (%) |
| --- | --- | --- |
| 9 | −12.8 | 63.4 |
| 30 | −11.2 | 75.2 |
| 300 | −10.5 | 80.2 |

According to the results, it was shown that when the enzyme was used in a too high amount or too low amount, the obtained composite particles had a surface charge of less than −10 mV and an antibacterial rate of less than 90%.

Comparative Example 1

A glucose-based nanoparticle (with a molecular weight of $2.3*10^7$ g/mol and a dispersed molecular density of 1,230 g/(mol·nm$^3$)) derived from oysters was weighed and prepared into a homogeneous aqueous solution with a mass concentration of 40%. A microbial GH13 family amyloglucosidase that was 200 U/g of the substrate was added. Parameters of a reaction system were adjusted as follows: the temperature was 50° C., the pH was 7.0, and constant-temperature catalysis was conducted for 0.5 h. Succinic anhydride was added in an amount of 0.5% of a mass of the substrate, oxirene was added in an amount of 3% of the mass of the substrate, and the pH of a reaction system was adjusted to 12. Then, a microwave-assisted processing technology was used for adjusting a microwave power to 800 W to carry out a reaction at 50° C. for 6 h. Finally, precipitation and drying were conducted to obtain a target product.

The obtained target product had a surface zeta potential of −32.5 mV and a broad-spectrum antibacterial rate of 0%. It could be seen that the pure glucose-based nanoparticle had antibacterial activity of 0. In addition, by simply using a same amount of chitin to conduct an antibacterial experiment, it was found that the nanoparticle had a broad-spectrum antibacterial rate of 89.4%.

Comparative Example 2

A glucose-based nanoparticle (with a molecular weight of $2.3*10^7$ g/mol and a dispersed molecular density of 1,230 g/(mol·nm$^3$)) derived from oysters was weighed and prepared into a homogeneous aqueous solution with a mass concentration of 40%. A microbial GH13 family amyloglucosidase that was 200 U/g of the substrate was added. Parameters of a reaction system were adjusted as follows: the temperature was 50° C., the pH was 7.0, and constant-temperature catalysis was conducted for 0.5 h. Succinic anhydride was added in an amount of 0.5% of a mass of the substrate, oxirene was added in an amount of 3% of the mass of the substrate, and the pH of a reaction system was adjusted to 12. Then, a microwave-assisted processing technology was used for adjusting a microwave power to 800 W to carry out a reaction at 50° C. for 6 h. Next, chitin was added in an amount of 0.01% of the mass of the substrate to carry out a reaction by direct stirring at 20° C. for 0.5 h without an ultrasonic charge transfer process. Finally, precipitation and drying were conducted to obtain a target product.

The obtained target product had an average particle size of 625 nm, a surface zeta potential of −9.2 mV and a broad-spectrum antibacterial rate of 91.7%.

Comparative Example 3

With reference to Example 1, an organic acid anhydride was simply used for modification, 3% of oxirene was not added, and other conditions were unchanged.

A glucose-based nanoparticle (with a molecular weight of $2.3*10^7$ g/mol and a dispersed molecular density of 1,230 g/(mol·nm$^3$)) derived from oysters was weighed and prepared into a homogeneous aqueous solution with a mass concentration of 40%. A microbial GH13 family amyloglucosidase that was 200 U/g of the substrate was added. Parameters of a reaction system were adjusted as follows: the temperature was 50° C., the pH was 7.0, and constant-temperature catalysis was conducted for 0.5 h. Succinic anhydride was added in an amount of 0.5% of a mass of the substrate, and the pH of a reaction system was adjusted to 12. Then, a microwave-assisted processing technology was used for adjusting a microwave power to 800 W to carry out a reaction at 50° C. for 6 h. Next, chitin was added in an amount of 0.01% of the mass of the substrate, and a physical field charge transfer technology was used for adjusting an ultrasonic frequency to 100 kHz to carry out a reaction at 20° C. for 0.5 h. Finally, precipitation and drying were conducted to obtain a target product. The obtained target product had a broad-spectrum antibacterial rate of 83%.

What is claimed is:
1. A method of preparing an antibacterial glucose-based composite nanoparticle, comprising the following steps:
   (a) dispersing a natural glucose-based nanoparticle in water, and adding a microbial GH13 family glucoside hydrolase that is 50-200 U/g of the natural glucose-based nanoparticle to conduct a catalytic reaction;
   (b) after the catalytic reaction is completed, adding an organic acid anhydride esterification agent and an etherification agent, adjusting the pH to 7-13 and performing a second reaction by exposure to microwave energy; and (c) after the second reaction is completed, adding a preservative of 0.01-1% by mass of the natural glucose-based nanoparticle and performing a third reaction by exposure to ultrasound, and then conducting precipitation and drying;

wherein, the preservative comprises one or more selected from the group consisting of nisin, lysozyme, and chitin.

2. The method according to claim 1, wherein, the natural glucose-based nanoparticle has a molecular weight of $10^6$-$10^8$ g/mol and a dispersed molecular density of 1,000-2,000 $g \cdot mol^{-1} \cdot nm^{-3}$.

3. The method according to claim 1, wherein, in step (a), the natural glucose-based nanoparticle in the water has a mass concentration of 10-40%.

4. The method according to claim 1, wherein, in step (a), the catalytic reaction is carried out at a constant temperature of 30-70° C. and a pH of 3.5-7.0 for 0.5-12 h.

5. The method according to claim 1, wherein, in step (b), the organic acid anhydride esterification agent is added in an amount of 0.5-3% of the mass of the natural glucose-based nanoparticle.

6. The method according to claim 1, wherein, in step (b), the etherification agent is added in an amount of 1-10% of the mass of the natural glucose-based nanoparticle.

7. The method according to claim 1, wherein, in step (c), the ultrasound is conducted at an ultrasonic frequency of 20-100 kHz; and in step (c), the third reaction is carried out at 20-50° C. for 0.1-5 h to realize charge transfer.

8. The antibacterial glucose-based composite nanoparticle prepared according to claim 1.

* * * * *